United States Patent [19]

Shenoy

[11] 4,217,759

[45] Aug. 19, 1980

[54] CRYOGENIC PROCESS FOR SEPARATING SYNTHESIS GAS

[75] Inventor: Thirtahalli A. Shenoy, Spring Valley, N.Y.

[73] Assignee: Union Carbide Corporation, New York, N.Y.

[21] Appl. No.: 24,598

[22] Filed: Mar. 28, 1979

[51] Int. Cl.² .............................................. F25J 3/02
[52] U.S. Cl. .......................................... 62/27; 62/23; 62/38
[58] Field of Search ............................ 62/23, 24, 27, 28

[56] References Cited
U.S. PATENT DOCUMENTS

| | | | |
|---|---|---|---|
| 3,359,744 | 12/1967 | Bolez et al. ............................... | 62/36 |
| 3,508,413 | 4/1970 | Pryor ........................................ | 62/24 |
| 3,553,972 | 1/1971 | Markbreiter et al. ................... | 62/23 |
| 3,872,025 | 3/1975 | Singleton ................................. | 62/23 |
| 3,929,438 | 12/1975 | Harper et al. ........................... | 62/28 |

*Primary Examiner*—Norman Yudkoff
*Attorney, Agent, or Firm*—John C. LeFever

[57] ABSTRACT

A cryogenic separation of a feed gas mixture comprising hydrogen, carbon monoxide and methane by partial condensation, in which the feed gas is partially cooled and condensed, then separated to form first gas and liquid fractions, the latter is separated into carbon monoxide product gas and methane product gas, and the first gas fraction is further cooled for additional partial condensation and separated into a hydrogen enriched gas fraction and a second carbon monoxide rich liquid.

10 Claims, 7 Drawing Figures

CRYOGENIC PROCESS FOR SEPARATING SYNTHESIS GAS

BACKGROUND OF THE INVENTION

This invention relates to a cryogenic process for separating synthesis gas by partial condensation.

Synthesis gas is commonly produced in the chemical processing industry by a variety of techniques, for example, the steam reforming of natural gas (methane), and the pyrolysis or partial oxidation of both solid and liquid hydrocarbon feedstocks. The so-produced synthesis gas mixture contains the desired hydrogen and carbon monoxide products, as well as residual methane. By way of example, the synthesis gas mixture may contain approximately 40 to 70 mole % hydrogen, 15 to 60 mole % carbon monoxide, 0.1 to 15 mole % methane and the remainder argon and nitrogen. Consistent with the use of the synthesis gas constituents as chemical precursors, the three major components are separated and purified to the required degree. Both cryogenic and noncryogenics processes are available to provide the required separations and each offer their own advantages. The present invention is concerned primarily with the cryogenic approach.

In the past, there have been two basic cryogenic approaches to the complete separation of synthesis gas; the methane wash approach and the partial condensation - pressure swing adsorption approach. In the methane wash approach, a synthesis gas feed stream is provided at elevated pressure and cooled to form a vapor-liquid mixture which is introduced to the methane wash column. Prior to the methane wash column, the feed gas stream may undergo a preliminary separation by partial condensation to increase its hydrogen content. In the wash column, the feed is contacted with a high purity, sub-cooled methane wash liquid for absorption of feed carbon monoxide into the methane wash liquid. High purity hydrogen product is recovered from the overhead of the methane wash column and liquid containing the wash methane and absorbed carbon monoxide is recovered in the bottoms. Recovered bottoms liquid is then throttled to reduced pressure and fractionated in a carbon monoxide separation column. This column produces an overhead carbon monoxide product and a high purity methane bottoms liquid. A portion of the methane bottoms is then subcooled and recycled as wash liquid for the methane wash column.

Current examples of the methane wash approach are those described in Allam et al. U.S. Pat. No. 3,86,756 and Martin U.S. Pat. No. 4,102,659. In such systems, the final hydrogen purification is done within the cryogenic equipment by absorbing heavy components from the light stream with a subcooled methane wash stream. The high purity methane wash stream is generated in the carbon monoxide separation column where the binary separation of carbon monoxide from methane is conducted. Because of the necessity for generating a sizable, sub-cooled liquid methane wash stream, these processes tend to be very energy intensive. Moreover, these systems are also limited to synthesis gas feeds having low carbon monoxide to methane molar ratios, e.g., less than about 30 and preferably lower. At higher carbon monoxide to methane molar ratios, the power requirements associated with refrigeration and the complexity associated with this approach cannot normally be justified relative to the partial condensation - PSA approach.

A typical commercially practiced prior art system employing the partial condensation approach to synthesis gas processing represented by Pryor U.S. Pat. No. 3,508,413 (FIG. 1). In the Pryor process, the synthesis gas is first cooled and partially condensed in a first heat exchanger and the condensed liquid fraction is separated from the vapor fraction. This first separation occurs at an intermediate cryogenic temperature and reduces the amount of hydrogen which is subsequently dissolved in the liquid phase produced upon complete cooling. Earlier less efficient prior art approaches cooled the feed gas stream directly to the temperature at the cold end of the system. This dissolves a large amount of hydrogen in the liquid phase subsequently recovered, and results in substantial difficulty in separating this dissolved hydrogen from the final carbon monoxide product.

The non-condensed feed gas recovered from the first separator is then further cooled in a second lower temperature heat exchanger and a hydrogen enriched gas is separated from a carbon monoxide rich liquid in a coldest temperature separator. The hydrogen rich gas from this separation is then partially warmed in the second heat exchanger, expanded through a turbine to develop refrigeration for this system and then its sensible refrigeration is consecutively removed through the second and first heat exchangers respectively. The liquid recovered from the first separator with liquid from an intermediate temperature separation are thereafter throttled into a lower pressure separator. Similarly, the hydrogen saturated liquid recovered from the lowest temperature separator is partially reboiled in the lowest temperature heat exchanger and is throttled into still another separator. The hydrogen saturated liquid fractions subsequently recovered from both separators are expanded into a carbon monoxide-methane separation column. The overhead saturated vapor streams recovered from each of these separators are combined, warmed in the first heat exchanger and then recycled to join the synthesis feed gas. It should be noted that one portion of the saturated liquid from the last-mentioned separator is flashed into a subatmospheric pressure separator. This operation provides an additional source of refrigeration for the system. The patentee also claims that this step greatly increases the thermal efficiency of the cycle and therefore greatly reduces the power requirements of the process by reducing the temperature difference at both the warm and cold ends of the first heat exchanger. The liquid recovered from the subatmospheric pressure separator is fed to the carbon monoxide-methane separation column while the vapor separated is passed to the carbon monoxide product stream. Reboil for the carbon monoxide-methane separation column is provided by heat exchange with the cooling synthesis feed gas stream. The column produces a methane-enriched fuel gas bottoms product and the high purity carbon monoxide overhead product.

A prior art modification of the Pryor partial condensation system is illustrated in FIG. 1. The synthesis gas supplied at super atmospheric pressure is supplied through conduit 11 and first cooled and partially condensed in first heat exchanger 12, and the condensed liquid fraction is separated from the vapor fraction in first separator 13. The non-condensed vapor fraction is passed through conduit 14 for further cooling in second lower temperature heat exchanger 15 and a hydrogen enriched gas is separated from a carbon monoxide rich liquid in lowest temperature separator 16. The hydrogen rich gas in conduit 17 is then partially rewarmed in heat exchanger 15, expanded through turbine 18 to develope refrigeration for the system and passed back through heat exchangers 15 and 12 for recovery of sensible refrigeration.

The hydrogen-saturated first liquid fraction is discharged from first separator 13 into conduit 19 and throttled through valve 20 into first lower pressure separator 21. The throttled low pressure carbon monoxide enriched gas is discharged through conduit 22 for sensible refrigeration recovery in first heat exchanger 12. The throttled carbon monoxide and methane enriched liquid is passed through conduit 23 to an intermediate level of carbon monoxide-methane separation column 24.

The carbon monoxide-enriched liquid fraction from coldest separator 16 is discharged through circuit 25, throttled in valve 26 and partially rewarmed (reboiled) in lower temperature heat exchanger 15 before entering second lower pressure separator 27. The carbon monoxide enriched gas from the latter is discharged therefrom in conduit 28 and joins gas from conduit 22 in combination conduit 29 for recovery of sensible refrigeration in first heat exchanger 12. The carbon monoxide rich liquid fraction from second lower pressure separator 27 is passed through bottom conduit 30 into the top end of carbon monoxide-methane separation column 24 as reflux liquid.

Heat for driving the lower end of column 24 is provided by a warmer fluid in reboiler 31, as for example, a partially cooled portion of the synthesis feed gas (not illustrated). The methane rich bottoms liquid from column 24 is withdrawn through conduit 33 and passed through first heat exchanger 12 for recovery of latent refrigeration. The high purity carbon monoxide overhead product gas from column 24 is discharged through conduit 32 and passed to first heat exchanger 12 for recovery of its sensible refrigeration.

The main difference between the Pryor and FIG. 1 prior art partial condensation systems is that the latter eliminates the intermediate temperature separator and the sub-atmospheric pressure separator along with the associated valves and piping.

There are two principle disadvantages of both of these prior art partial condensation systems. Firstly, the carbon monoxide rich liquid fraction from the lowest temperature separator 16 passes through second lowest pressure separator 27 and is coupled directly to separation column 24, i.e. the operating pressure of separator 27 dictates the maximum operating pressure of the column. Since a low pressure warming stream yields a desirable reboiling characteristic in lower temperature heat exchanger 15, with the use of a low recycle flow, the bottoms from separator 16 must be flashed to a low pressure. Accordingly, the carbon monoxide-methane separation column must also operate at a low pressure. Attempts at processing stream 25 at higher pressures result in a higher recycle flow and subsequently higher recycle compression requirements, as well as a performance degradation in lower temperature heat exchanger 15.

The second deficiency of these prior art partial condensation systems relates to throttling of the hydrogen saturated liquid from first separator 13 into lower pressure separator 21. This throttling step is conducted at a low pressure to insure complete removal of hydrogen. However, this also results in a high carbon monoxide loss into the overhead vapor, thereby greatly increasing the power requirements due to recycle compression.

A further limitation of these prior art partial condensation processes is that they cannot be adapted to separation of synthesis gas mixtures having carbon monoxide to methane molar ratios below about 10. This is because they cannot optimally balance the competing requirements of refrigeration, product recovery and purity.

An object of this invention is to provide an improved cryogenic process for separating synthesis gas by partial condensation, in which the operation of the carbon monoxide-methane separation is uncoupled from the low pressure reboiling carbon monoxide stream in the lower temperature heat exchanger.

Another object is to provide such a process which permits operation of the carbon monoxide-methane separation column at the optimum pressure without sacrificing overall process efficiency.

Still another object is to provide an improved cryogenic process for separating synthesis gas by partial condensation, which process requires substantially less total power than presently available partial condensation processes.

An additional object is to provide such a process which extends the advantages of the partial condensation approach for synthesis gas separation to feed gas streams having carbon monoxide to methane molar ratios below about 10.

Other objects will be apparent from the ensuing disclosure and appended claims.

SUMMARY

This invention relates to a cryogenic process for separating synthesis gas by partial condensation.

More specifically the invention relates to the cryogenic separation of a gas mixture comprising hydrogen, carbon monoxide and methane by partial condensation, in which the feed gas mixture is provided at super atmospheric pressure above about 300 psia and partially cooled to condense a first liquid fraction and recover a first gas fraction, the first liquid fraction is separated into a carbon monoxide product gas and methane product liquid, the first gas fraction is further cooled for additional partial condensation and separated into a hydrogen enriched gas fraction and a second carbon monoxide rich liquid.

The invention improvement comprises: (a) treating said first liquid fraction so as to provide a carbon monoxide rich liquid feed to the carbon monoxide-methane separation; (b) further cooling the first gas fraction at about said super atmospheric pressure for additional partial condensation and separating the same into a second liquid fraction and a second gas fraction as said hydrogen enriched gas; (c) rewarming said second gas fraction as said hydrogen enriched gas fraction by heat exchange initially with the further cooling first gas fraction and thereafter with the partially cooling feed gas mixture; (d) expanding said second liquid fraction to lower pressure between 20 psia and 130 psia, and separating the same into a third liquid fraction and a third gas fraction; (e) providing said third gas fraction at low super atmospheric pressure below about 50 psia; (f) providing a minor portion of a carbon monoxide rich liquid obtained from the cooled feed gas mixture after further cooling, at said low super atmospheric pressure of step (e) and combining said minor portion with the so-provided third gas fraction to form a recycle mixture; (g) rewarming said recycle mixture by heat exchange initially with the further cooling first gas fraction and thereafter with the partially cooling feed gas mixture; and (h) flowing at least a major portion of said third liquid fraction to the carbon monoxide-methane separation.

In this invention the first liquid fraction may be treated in any of several modes so as to provide carbon monoxide rich liquid feed to the carbon monoxide-methane separation. One mode illustrated in FIG. 2 is to first throttle the liquid to a lower super atmospheric pressure between 20 psia and 130 psia and then separate the throttled fluid into a liquid fraction which is fed to the carbon monoxide-methane separation, and a gas fraction. The latter is heat exchanged with the feed gas mixture for cooling thereof, and may be at least partially recycled by mixing with the feed gas prior to cooling and partial condensation thereof.

In a second mode for treating the first liquid fraction illustrated in FIG. 3, the latter is first throttled and the resulting fluid is separated as in the first mode, but the throttled liquid fraction is further cooled and throttled. The resulting fluid is separated into gas and liquid fractions. At least part of the latter is partially rewarmed against the first gas in the further cooling step and fed to the carbon monoxide-methane separation. The gas fraction recovered from the further cooled fluid separation is also partially rewarmed by heat exchange with the first gas in the further cooling step, and further rewarmed by heat exchange with the feed gas mixture in the partial cooling-condensation step.

In a third mode for treating the first liquid fraction to provide carbon monoxide-rich liquid as illustrated in FIG. 4, the former is first throttled and separated, and the liquid is then further cooled again and throttled and separated as in the second mode. However the final liquid fraction is only partially rewarmed by the first gas in the further cooling step. The resulting partially rewarmed liquid fraction is again separated to provide still further gas and liquid fractions. The latter is further rewarmed and reboiled, and passed to the carbon monoxide-methane separation as the carbon monoxide rich liquid feed, and the partially rewarmed gas is further warmed against the cooling feed gas mixture in the partial cooling step.

In a fourth mode for treating the liquid fraction to provide carbon monoxide rich liquid as illustrated in FIG. 5, the first liquid fraction is further cooled in the same further cooling step as the first gas, and then throttled to a lower super atmospheric pressure. The resulting fluid is separated into gas and liquid fractions, and the latter is partially reboiled in the aforementioned further cooling step against the first liquid and gas fractions. The resulting fluid is passed to the carbon monoxide-methane separation. The gas is rewarmed for recovery of its sensible refrigeration, first in the further cooling heat exchange against the first gas and the first liquid fraction, and then in the feed gas partial condensation step.

In step (f) of this process, a minor portion of a carbon monoxide-rich liquid obtained from the cooled feed gas mixture after the further cooling step is provided at the low super atmospheric pressure of the throttled third gas fraction from step (e). This carbon monoxide rich liquid may be provided by diverting a minor part of the third liquid fraction as for example illustrated in FIGS. 2 through 4. Alternatively, the carbon monoxide-rich liquid may be derived from the first liquid fraction as illustrated in FIG. 5.

BRIEF DESCRIPTION OF THE DRAWINGS

Where appropriate, corresponding elements in the various Figures are identified by numbers with the same last two digits.

Referring to FIG. 2, a synthesis feed gas having carbon monoxide to methane molar ratio greater than 60 is supplied to conduit 111 at super atmospheric pressure above about 300 psia and first cooled and partially condensed in first heat exchanger 112 by five colder fluids discussed hereinafter. The resulting fluid mixture is passed to first separator 113, and separated into a first gas fraction in conduit 114 and first liquid fraction in conduit 119. The first gas fraction is further cooled and additionally partially condensed in second lower temperature heat exchanger 115 by four colder fluids discussed hereinafter, and passed to second separator 116. The second hydrogen-rich vapor from separator 116 in conduit 117 is partially rewarmed in second heat exchanger 115, expanded through turbine 118 to develop refrigeration for the system and then again rewarmed in second heat exchanger 115 and finally in first heat exchanger 112 before discharge from the system. The hydrogen-saturated liquid recovered from second separator 116 in conduit 125 is throttled through valve 126 and the resulting gas-liquid is passed to third separator 145 at the cold end of the system.

Figure 1:
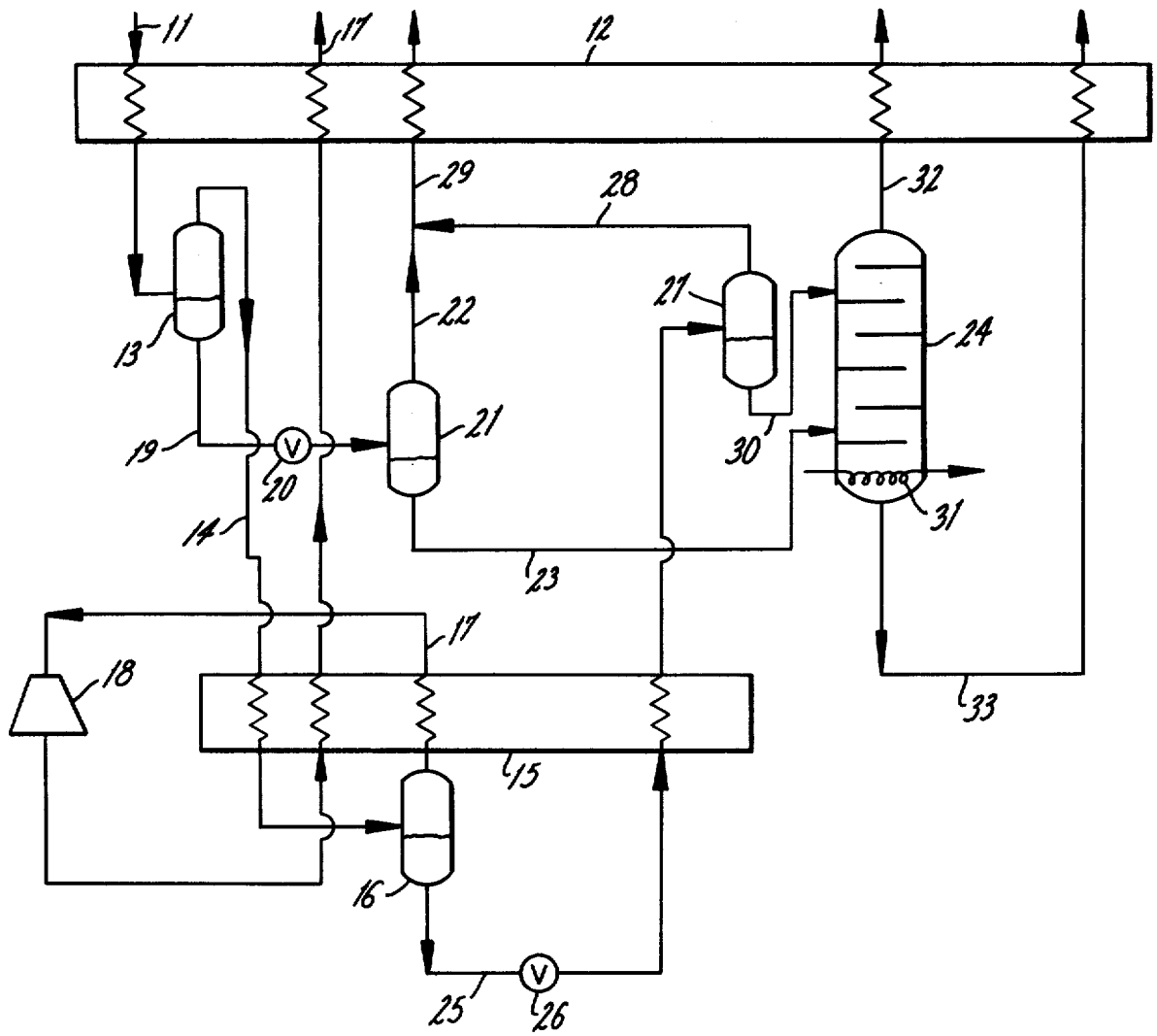
FIG. 1 is a schematic drawing of apparatus suitable for practicing a prior art cryogenic process for separating synthesis gas by partial condensation.

A major part of the carbon monoxide-rich liquid recovered from third separator 145 in conduit 146 is partially reboiled in second heat exchanger 115 and fed to the upper part of carbon monoxide-methane separation column 124 as wash liquid. The other minor part of the cold carbon monoxide-rich liquid is diverted to conduit 147 upstream second heat exchanger 115, and throttled through valve 147 to low super atmospheric pressure below about 50 psia. A third gas fraction is released from third separator 145 through conduit 149 and throttled in valve 150 to low super atmospheric pressure below about 50 psia, whereupon the diverted throttled carbon monoxide rich fluid in conduit 147 is joined therewith to form a low pressure recycle mixture in conduit 151. The latter is reboiled and rewarmed initially by heat exchange with the further cooling and additionally partially condensing first gas fraction in second heat exchanger 115 and thereafter additionally rewarmed with the partially cooling and condensing feed gas mixture in first heat exchanger 112. The resulting warmed low pressure gas in conduit 149 may be recompressed and recycled as part of the feed gas mixture in conduit 111 by means not shown. By reboiling the conduit 151 portion of the recycle stream at a significantly lower pressure than the prior art (below about 50 psia), the heat transfer characteristics for this stream in second exchanger 115 are optimized. Also, this low pressure recycle stream is not passed to the carbon monoxide-methane separation column 124 and the latter may be operated at the desired higher pressure.

Returning now to the first liquid fraction 119 discharged from first separator 113, it is treated to provide carbon monoxide-rich liquid feed to column 124 by first throttling in valve 120 to a pressure level commensurate with the pressure for carbon monoxide-methane separation column 124, i.e. between 20 and 130 psia. The resulting throttled fluid is separated in fourth separator 121 to form a gas fraction in overhead conduit 122 and a liquid fraction in conduit 123. The former is rewarmed in first heat exchanger against the cooling feed gas mixture, and may be recycled (by means not illustrated) to feed gas conduit 111. The throttled liquid fraction flows through conduit 123 and control valve 153 to column 124 as the carbon monoxide-rich liquid feed. As previously explained, column 124 may be advantageously operated at a substantially higher pressure than possible with the prior art systems. Also, the column operating pressure is significantly higher than the desirably low pressure recycle gas stream in conduit 151. These improvements permit a sizeable reduction in the total power requirements for this invention.

A high purity carbon monoxide overhead product gas is discharged through conduit 132 and warmed in first heat exchanger 112 against the cooling synthesis feed gas, and methane-rich bottoms liquid is withdrawn through conduit 133 with control valve 134 therein. The refrigeration value of this stream is recovered in first heat exchanger 112.

Figure 2:
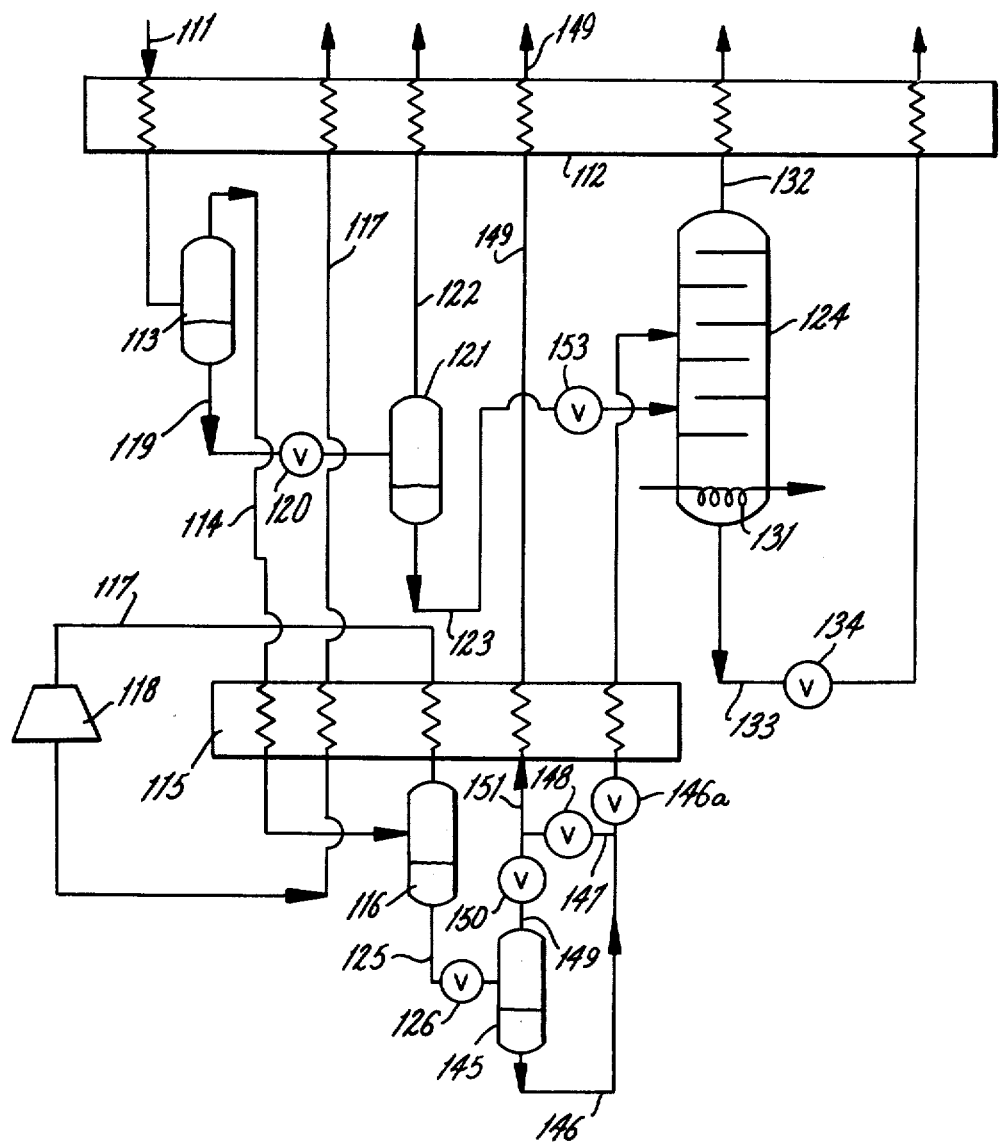
FIG. 2 is a schematic drawing of apparatus suitable for practicing the inventive process with synthesis feed gas having carbon monoxide to methane molar ratio greater than 60, in which carbon monoxide rich liquid feed for the carbon monoxide-methane separation is obtained from the first liquid fraction by throttling and separation.

A comparison of the prior art FIG. 1 process and the FIG. 2 process of this invention is provided by the examples of Table A. In each case, the system processes 1000 lb.mole/hr. of a feed gas having a hydrogen content of 44.7%, a carbon monoxide content of 54.74% and a methane content of 0.26% with the remaining gases comprising nitrogen and argon at a pressure of 500 psia and temperature of 278° K. The feed gas is cooled to 103° K. in the first exchangers and the first gas further cooled to 72° K. in the second exchangers. There are two hydrogen product streams discharged from the first exchanger warm end after turbine expansion in the FIG. 6 manner. They are at 335 psia and 180 psia in both FIGS. 1 and 2. In FIG. 1 the column operates at 54 psia whereas in FIG. 2 the column operates at a more efficient level of 80 psia. By utilizing this invention one can produce a carbon monoxide product at a similar purity and recovery while realizing an 11% decrease in power requirement (based on carbon monoxide product). As shown in Table A, this power requirement is derived from a reduction in the requirement for product compression. In the FIG. 2 approach, carbon monoxide product is produced at 54 psia, while utilizing the present invention the carbon monoxide product is recovered at 80 psia.

TABLE A

PERFORMANCE SUMMARIES

Figure 3:
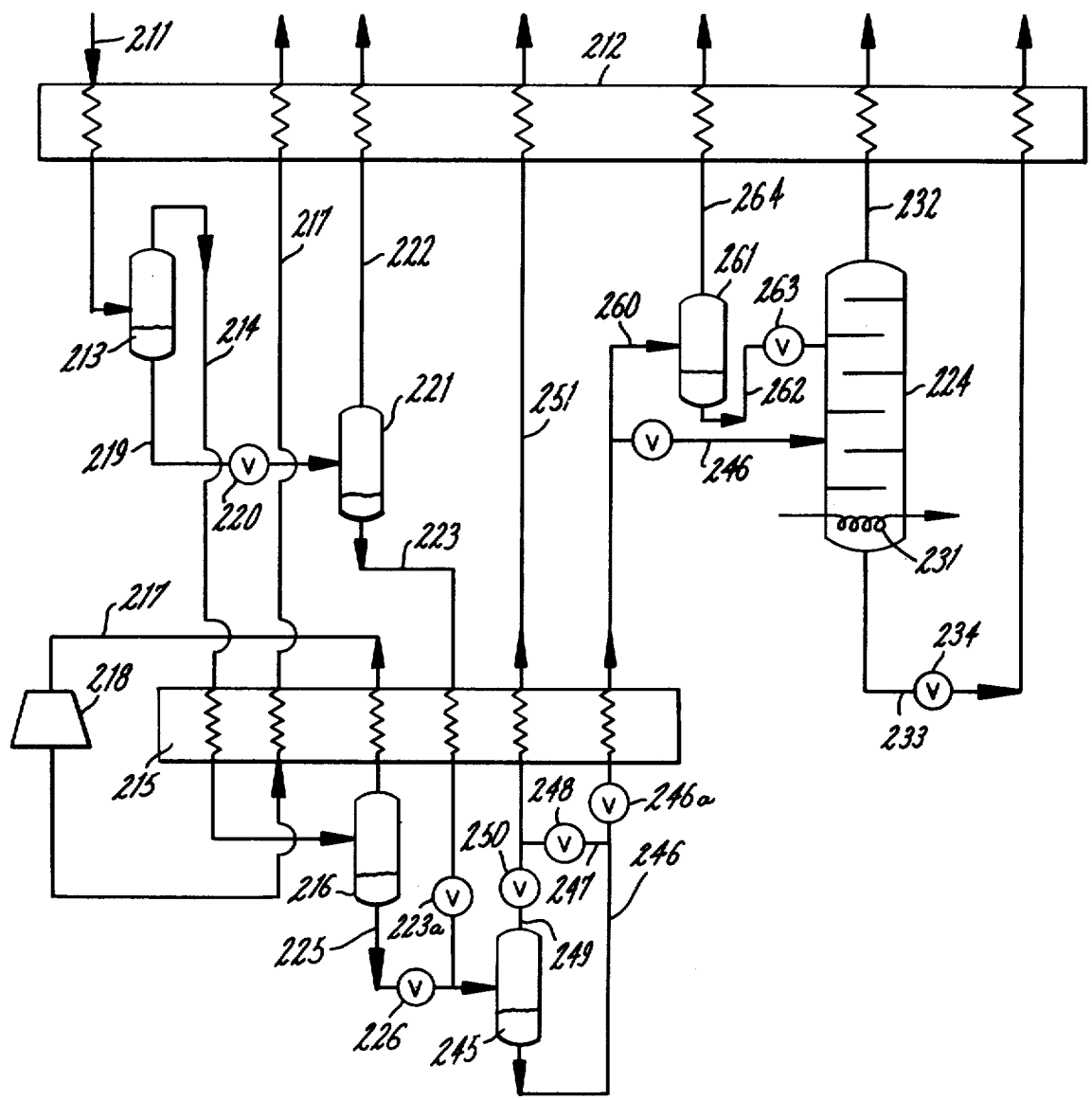
FIG. 3 is a schematic drawing of apparatus suitable for practicing another embodiment of the invention similar to FIG. 2, but with further cooling of the throttled liquid fraction from which carbon monoxide rich liquid is derived by rewarming.
Figure 4:
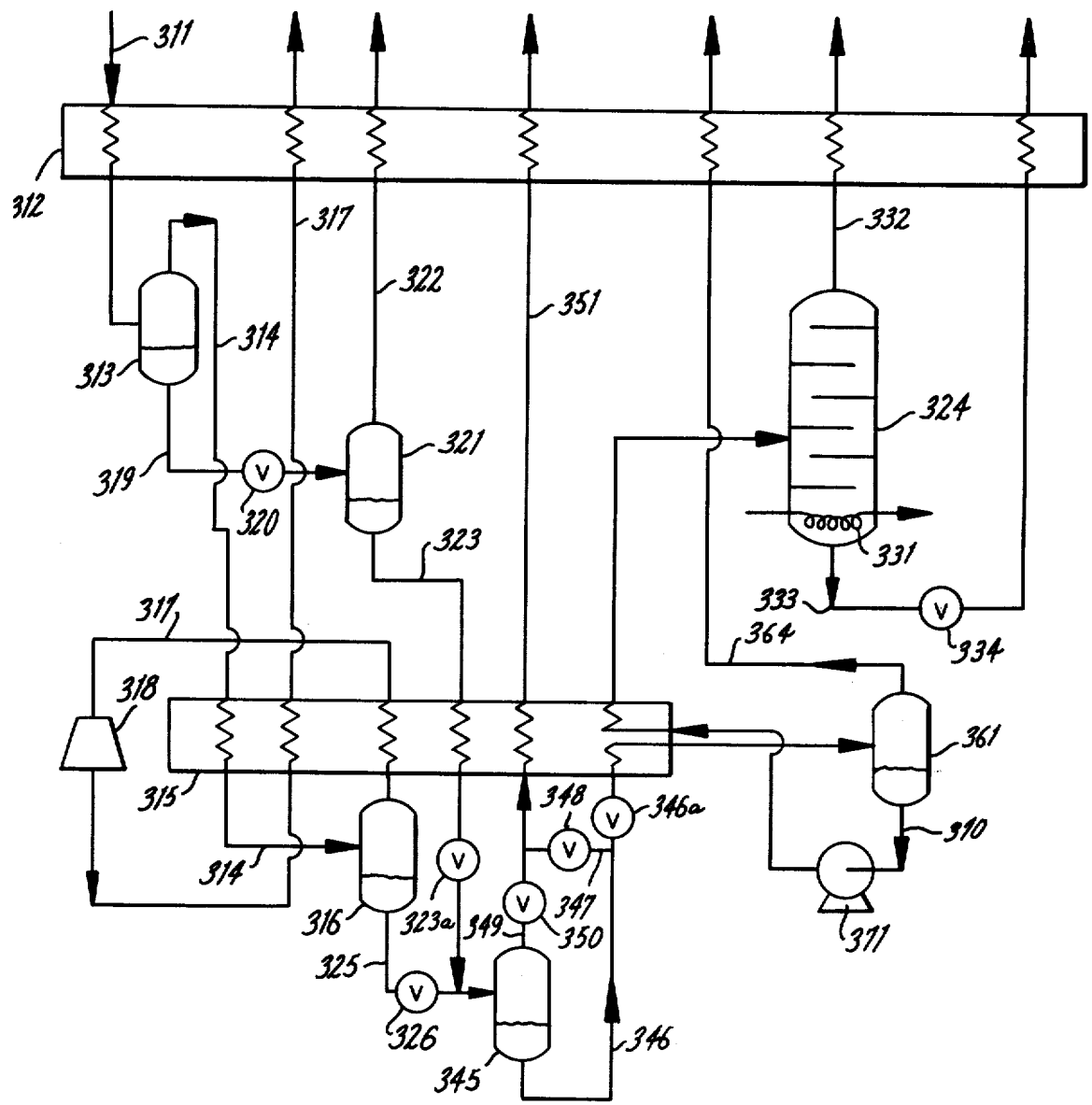
FIG. 4 is another embodiment similar to the FIG. 3 embodiment, in which the final liquid fraction from the further cooled and throttled fluid is only partially rewarmed before entering the carbon monoxide-methane separation.
Figure 6:
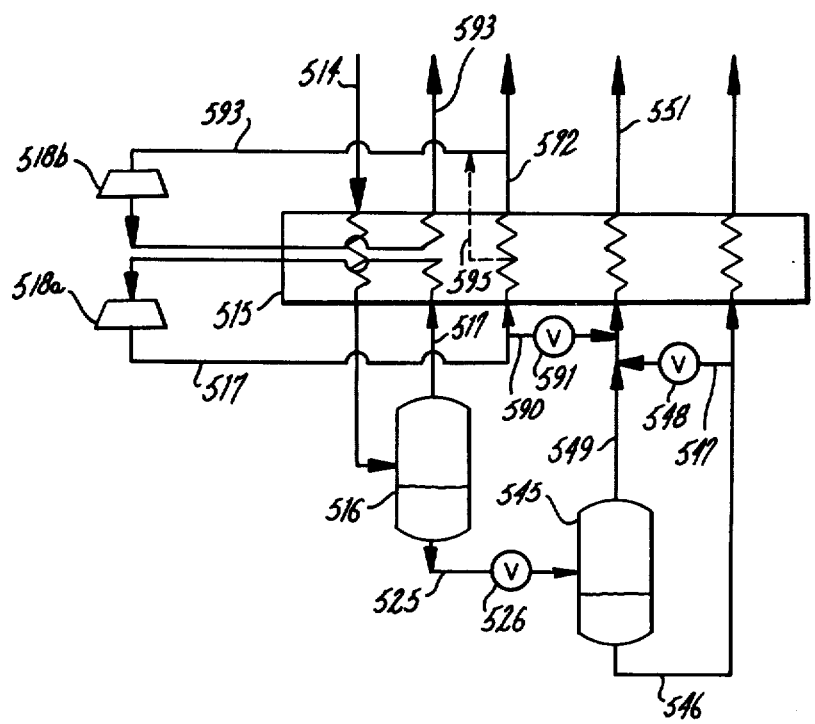
FIG. 6 is a schematic drawing of apparatus suitable in the FIGS. 2 through 5 and 7 embodiments for practicing hydrogen expansion in two gas turbines with hydrogen backmix.

| | FIG. 1 | FIG. 2 | FIG. 3 | FIG. 4 |
|---|---|---|---|---|
| Feed Rate (lb.moles/hr.) | 1000 | 1000 | 1000 | 1000 |
| CO Product Purity (Mole %) | 99.30 | 99.24 | 99.27 | 99.23 |
| Total Power (kw/lb.mole CO Product) | 1.73 | 1.54 | 1.55 | 1.45 |
| Recycle Compressor* (kw/lb.mole CO Product) | 0.66 | 0.68 | 0.70 | 0.60 |
| Product Compressor** (kw/lb.mole CO Product) | 1.07 | 0.86 | 0.85 | 0.85 |
| Type of Hydrogen Expansion and Backmix | FIG. 6 1st method | FIG. 6 1st method | FIG. 6 1st method | FIG. 6 2nd method |

*Compression to 320 psia
**Compression to 480 psia

The FIG. 3 embodiment differs in certain respects from FIG. 2, and these differences offer advantages. In FIG. 3, expansion of the first liquid fraction from separator 213 through conduit 219 and valve 220 into fourth separator 221 is conducted at a higher pressure level than in the FIG. 2 system, e.g., at 320 psia as compared with 85 psia. The hydrogen saturated liquid recovered in separator 221 is then passed through conduit 223, subcooled in second heat exchanger 215, and flashed into third separator 245 along with the hydrogen saturated liquid recovered from second separator 216 in conduit 225. By subcooling the saturated liquid recovered from fourth separator 221, a higher carbon monoxide recovery in the liquid phase is achieved when this liquid is flashed into third separator 245. The liquid from third separator 245 is then processed in a manner analogous to FIG. 2 approach with a minor portion being throttled through conduit 247 and valve 248, and reboiled with the overhead gas from third separator 245 in conduit 251. The major other portion of the third separator liquid is throttled through valve 246a and then partially reboiled in second lower temperature heat exchanger 215. A portion of this reboiled liquid can then be fed directly into column 224 through conduit 246 as part of the carbon monoxide-rich liquid, while the other portion can be fed through conduit 260 to fifth separator 261 for a preliminary separation, with the saturated carbon monoxide-rich liquid recovered in conduit 262 forming the other feed to the carbon monoxide-methane separation column 224. As such, the vapor recovered from fifth separator 261 in conduit 264 represents the final point for hydrogen rejection from the column 224 feeds and offers flexibility in controling the hydrogen impurity level in the carbon monoxide product. This option, however, must be viewed with respect to the power penalty one suffers with the higher recycle flow so produced.

Table A also compares FIG. 3 with FIG. 2 embodiment and the FIG. 1 prior art system. The CO product purity is slightly higher than FIG. 2, and the total power consumption is about the same. The column operates at 82 psia and there are three recycle gas streams: the high pressure gas in conduit 222 at 320 psia comprising 8% of the total, the intermediate pressure gas in conduit 264 at 84 psia comprising 26%, and the lower pressure gas in conduit 251 at 28 psia comprising 66% of the total.

The FIG. 3 embodiment, although representing a means for improving carbon monoxide product purity as shown in Table A, represents a relatively inefficient manner for final rejection of hydrogen impurities prior to carbon monoxide-methane separation column 224. As previously stated, fifth separator 261 can be used as the final rejection point of the hydrogen which has been dissolved in the carbon monoxide at the cold end of the process. However, almost twenty times as much carbon monoxide is rejected along with the hydrogen, and the CO must subsequently be recycled. As a result, the FIG. 3 embodiment requires slightly more power than the FIG. 2 embodiment. It would be highly advantageous if the impurity hydrogen could be removed without significantly increasing recycle flows. This problem has been solved in the FIG. 4 embodiment by performing this final separation of the hydrogen impurity from the carbon monoxide-rich liquid recovered from the third separator at a lower temperature and a much lower pressure than in the FIG. 3 embodiment.

Referring now to FIG. 4, the major portion of the carbon monoxide-rich liquid recovered from third separator 345 in conduit 346 for subsequent feeding to column 324 is throttled through valve 346a to a very low pressure, i.e., below 50 psia and, is partially reboiled in second lower temperature heat exchanger 315. The partially reboiled stream is then passed to fifth separator 361. The liquid from separator 361 in conduit 370 is then pressurized to the column 324 operating level by means of liquid pump 371 and returned to heat exchanger 315 at the point of withdrawal of the saturated liquid from separator 345 for additional reboiling and introduction to the column as the carbon monoxide-rich feed. The hydrogen saturated vapor from fifth separator 361 in conduit 364, now at a greatly reduced flow rate, is warmed in heat exchanger 312 and passed to the feed recycle compressor through conduit 364.

Fortuitously, the aforedescribed unique features of the FIG. 4 embodiment also solve a potential problem of the FIG. 3 embodiment involving the stability of the recycle flow. Referring to FIG. 3, it can be seen that any fluctuation in the temperature of the separation in first separator 213 will produce fluctuations in warm end exit temperatures in lower temperature heat exchanger 215. Such fluctuations will produce subsequent fluctuations in the flow rate of vapor from fifth separator 261, i.e., the recycle flow. In the FIG. 4 system, however, any fluctuations in the temperature of separator 361 produced by fluctuations in the temperature of first separator 313 will be negligible because the temperature level of withdrawal is near the mid point of heat exchanger 315 rather than from the warm end. In any event this will have negligible impact on the total recycle gas flow since the vapor flow from separator 361 is inherently small and negligible in comparison to the vapor flow from separator 264 in FIG. 3. For example, in the illustrative case presented in Table A, the saturated vapor flow from separator 261 in the FIG. 3 system is about ten times greater than the saturated vapor flow from separator 361 in the FIG. 4 system.

Even though separator 361 in the FIG. 4 embodiment is operated at a much lower pressure than separator 261 in the FIG. 3 embodiment and thereby requires a higher recompression of the saturated vapor recovered therefrom prior to recycle, it has been found that the overall power requirements of the FIG. 4 system still is about 7% lower than the FIG. 3 system. Part of this advantage is realized by the reduction in the quantity of carbon monoxide that is lost by way of the overhead vapor from separator 361. This in turn reduces the total quantity of gas which must be recycled in the system and accordingly reduces the recycle compressor power requirements.

For the Table A comparison, the FIG. 4 column operates at 82 psia. There are two hydrogen product streams in the FIG. 6 manner, although only one stream is shown in conduit 317. The high pressure product hydrogen stream is at 335 psia and the low pressure product stream is at 220 psia. Of the three recycle gas streams, the high pressure gas in conduit 322 at 320 psia is 10.9% of the total, the low pressure gas in conduit 351 at 22 psia is 85.5% of the total, and the low pressure gas in conduit 364 is 3.6% of the total.

Figure 5:
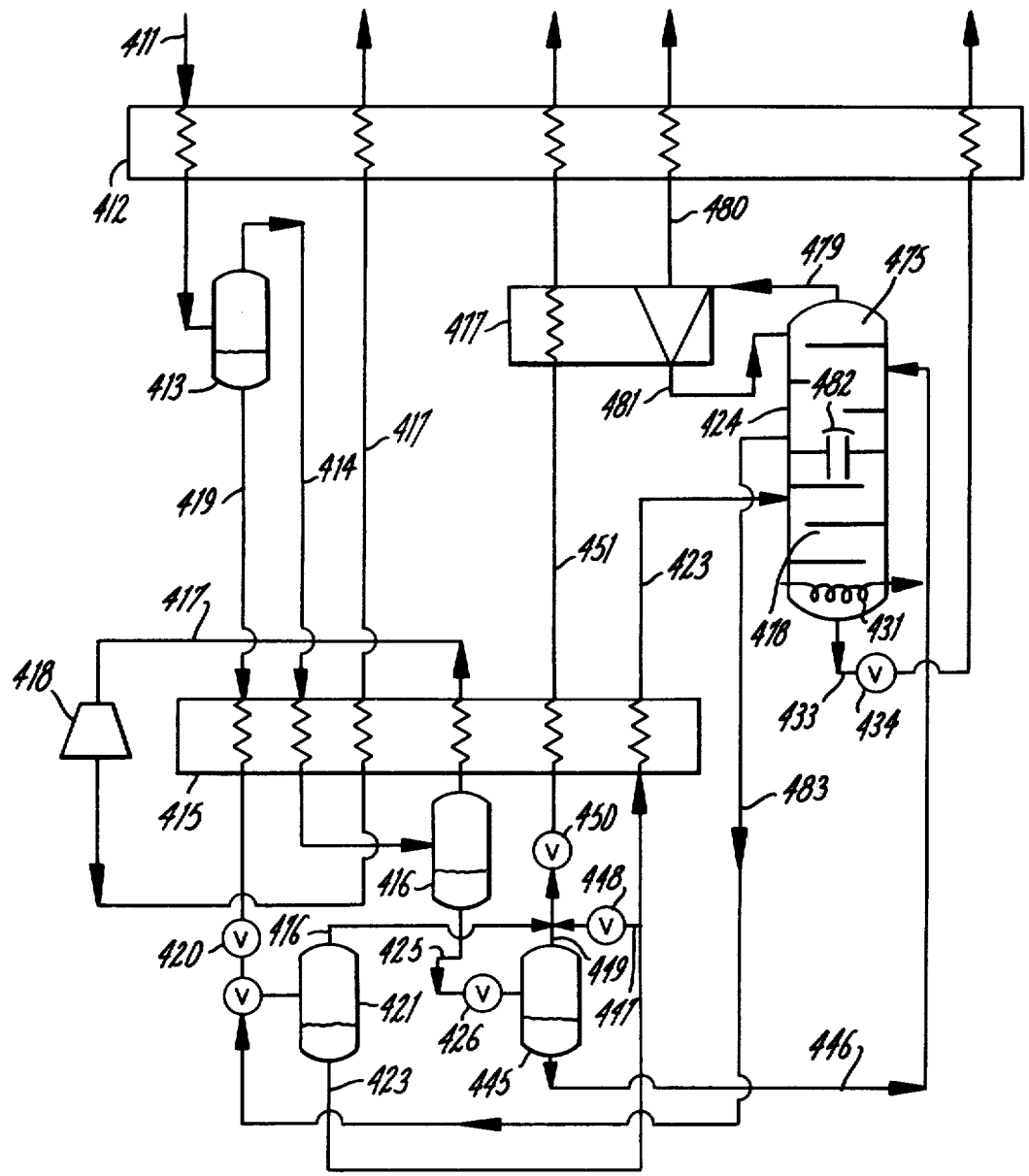
FIG. 5 is a schematic drawing of apparatus suitable for practicing an embodiment of the invention which is useful for separating synthesis gas feeds having a carbon monoxide to methane molar ratio between about 5 and 60.

The previously described embodiments are particularly suited to processing synthesis gas feeds having carbon monoxide to methane molar ratios above about 60. In such systems, the carbon monoxide-methane separation column is relatively simple requiring only a partial reboiler without an overhead condenser. However, as the carbon monoxide to methane ratio is lowered, an overhead condenser is eventually required to maintain carbon monoxide product purities. Moreover, as this ratio is further reduced, both the complexity of the column and the complexity of the process must be increased to maintain product purities. FIG. 5 illustrates one embodiment of the invention which is useful for synthesis gas feeds having a carbon monoxide to methane molar ratio between about 5 and 60.

The feed gas in conduit 411 is initially cooled so as to partially condense a fraction thereof. The first gas fraction collected as overhead from first separator 413 in conduit 414 is then processed in a manner similar to the FIG. 4 embodiment. This gas is further cooled and additionally partially condensed in second lower temperature heat exchanger 415 and a hydrogen-enriched second gas fraction is separated therefrom in second separator 416 while the saturated liquid fraction recovered in conduit 425 is flashed through throttle valve 426 into third separator 445. The hydrogen-enriched second gas fraction in conduit 417 is partially warmed, expanded in turbine 418, and is then removed from the system sequentially through heat exchangers 415 and 412. The liquid expanded into third separator 445 is then separated into a vapor fraction and a saturated liquid fraction; the latter in conduit 446 forms a carbon monoxide-rich reflux liquid for the rectifying section 475 of the carbon monoxide-methane separation column 424 and is withdrawn directly from the cold end of the process.

Referring once again to first separator 413, the first liquid fraction in conduit 419 is further cooled (subcooled) in heat exchanger 415 and flashed through throttle valve 420 into separator 421. Liquid recovered from the lower portion of the rectifying section 475 of column 424 is also fed to lower pressure separator 421. The first saturated liquid fraction from the bottom of separator 413 is essentially equivalent to the saturated liquid recovered from fourth separator 121, 221, and 321 of the previous embodiments. The overhead vapor from separator 421 in conduit 476 is then mixed with the overhead vapor in conduit 449 from third separator 445 as well as with a conduit 447 diverted minor portion of the saturated liquid recovered from separator 421 in conduit 423, and the so-formed mixture is removed as a recycle stream through heat exchangers 415, 477 and 412 respectively. The major portion of the saturated liquid recovered from separator 421 in conduit 423 is partially reboiled in second heat exchanger 415 and then fed to the stripping section 478 of column 424. In the FIGS. 3 and 4 embodiments these streams (equivalent to the saturated liquids recovered from separator 421 and 445) were combined, partially reboiled and then fed to column 424. In this embodiment, it is important to keep them separate since the cold high purity carbon monoxide liquid recovered from separator 445 is needed as reflux for column 478 to insure carbon monoxide product purity. In the FIG. 5 embodiment, heat exchanger 477 comprises the reflux condenser for the rectifying section 475 of column 424. Overhead gas from this column is passed thereto from conduit 479 and is maintained in heat exchange against warming recycle gas mixture in conduit 451 so as to condense the major fraction of methane from the overhead. The uncondensed vapor portion is removed by conduit 480 through first heat exchanger 412 as product carbon monoxide. The condensed liquid fraction from heat exchanger 477 in conduit 481 is used as one portion of the reflux for the rectifying section 475 of column 424. The feed for the rectifying section 475 of column 424 comprises the upwardly flowing gas stream form the sripping section 478 which passes through tray 482. This tray is provided with a liquid catchment which prevents liquid flow into stripping section 478. The entire liquid downflow in section 478 is removed by conduit 483 as part of the feed to separator 421.

In the FIG. 5 embodiment it will be noted that a cold liquid is removed from the cold end of the system (liquid from separator 445) while a warmer liquid is returned (liquid from the rectifying section 475 of column 424 to separator 421) without any heat exchange. As a result the second gas discharged through conduit 476 to conduit 451 is undesirably warmed before entering heat exchanger 415. The latter stream may be cooled by an effect similar in nature to the Joule-Thompson effect produced by the addition of a hydrogen rich stream (for example stream 417) to a gas stream rich in carbon monoxide. In a preferred embodiment of this invention, a minor part of the second gas fraction from step (b) is diverted and mixed with the third vapor fraction of step (e) for further cooling prior to the rewarming of step (g). The addition of cold hydrogen to this stream (hereinafter referred to as hydrogen backmix) enhances the refrigeration recoverability at optimum temperatures from the recycle gas in heat exchanger 415.

FIG. 6 shows two methods for providing turbine expansion and hydrogen backmix. In one method, the solid lines are applicable and in the second method, the dashed-lines are applicable. Either of these methods may be used with the previously described embodiments. The first described method was used in the Table A comparisions for FIGS. 1, 2 and 3 while the second described method was used for FIG. 4. First gas (derived from feed gas) in conduit 514 is cooled in second heat exchanger 515 against rewarming exit streams and fed to second separator 516. The saturated liquid bottoms in conduit 525 is flashed through throttle valve 526 into separator 545. The overhead gas from third separator 545 comprises a recycle stream while the bottoms liquid from separator 545 in conduit 546 is rewarmed in second heat exchanger 515 and may for example be fed to the carbon monoxide-methane column. A small portion of the liquid in conduit 546 is passed through branch conduit 547 and valve 548 to be mixed with the overhead from separator 545.

Returning now to the overhead gas from second separator 516 in conduit 517, it is partially warmed in second heat exchanger 515 and withdrawn at an intermediate level such as the midpoint thereof, and expanded through first turbine 518a. The expanded gas is returned for further rewarming in second heat exchanger 515, while a portion thereof is withdrawn through conduit 590 and valve 591 to be mixed with the overhead gas from separator 545. This withdrawn stream constitutes the backmix hydrogen and serves to increase the efficiency of second lower temperature heat exchanger 515 by lowering the boiling point characteristics of the recycled stream in conduit 551. The remaining portion of gas exiting from first turbine 518a in conduit 592 is again rewarmed by passing through second heat exchanger 515 and is then fed to second turbine 518b through branch conduit 593 and expanded therethrough. The expanded gas is then fed to an intermediate level of heat exchanger 515 and is removed from this system through conduit 594.

In the second illustrated method for hydrogen expansion and backmix, one portion of the expanded gas in conduit 517 from first turbine 518a is fed to heat exchanger 515 while the remaining portion, as before, is diverted through conduit 590 and valve 591 therein as the backmix hydrogen stream. A portion of the first turbine expanded hydrogen gas feed to heat exchanger 515 is withdrawn at an intermediate level of heat exchanger 515 through conduit 595 and is fed to second turbine 518b through conduit 593. The remaining portion of the exhaust from first turbine 518a passes completely through second heat exchanger 515 and is withdrawn from the system through conduit 592. The hydrogen gas fed to second turbine 518b through conduit 593 is expanded therethrough, returned to an intermediate level of heat exchanger 515 and withdrawn in conduit 594.

The following is a working example of the present invention based on the FIG. 4 embodiment with the FIG. 6 hydrogen backmix.

EXAMPLE

One thousand lb. mole/hr. of a synthesis gas stream at 500 psia and 278° K. comprising on a molar basis 44.7% hydrogen, 54.7% carbon monoxide, 0.26% methane and the remainder nitrogen and argon is introduced through conduit 311, cooled to 104° K. in first heat exchanger 312 to thereby partially condense the gas mixture, and is thereafter separated in first separator 313. The saturated liquid from this separator, comprising a mixture containing on a molar basis 6.7% hydrogen, 92.2% carbon monoxide, 6.1% methane with the remainder nitrogen and argon, is removed through conduit 319 and is flashed through valve 320 and 320 psia and thereafter fed to separator 321. Overhead gas from separator 321 is discharged through conduit 322 flowing at 18.7 lb. mole/hr. and having a molar composition of 66.7% hydrogen, 33.0% carbon monoxide and 440 ppm of methane with the remainder comprising nitrogen and argon. The saturated liquid withdrawn through conduit 323 is cooled in second heat exchanger 315 to 74° K. and is thereafter expanded to 87 psia in valve 323a.

The first gas recovered in conduit 314 from first separator 313 is further cooled in heat exchanger 315 to a temperature of 74° K. for additional partial condensation and is then fed to second separator 316. The saturated liquid recovered from separator 316 in conduit 325 is flashed to 87 psia through valve 326, combined with the further cooled and throttled bottoms liquid from conduit 323 and the mixture is then fed to third separator 345. The overhead gas from second separator 316 in conduit 317 at 422 lb. mole/hr. and comprising 97% hydrogen and 3% carbon monoxide is rewarmed in heat exchanger 315 to 76° K., expanded through first turbine 518a to 345 psia and 70° K., and then divided into two streams. Seven lb. mole/hr. are used as backmix hydrogen by flashing the gas to 87 psia through conduit 590 and valve 591, and mixed with the overhead from separator 545. The remainder of the expanded hydrogen in conduit 517 is rewarmed in heat exchanger 515 to 76° K. and thereafter divided with 294 lbs. mole/hr. passing through conduits 595 and 593 to be expanded to 219 psia through second expander 518b, while the remainder is further rewarmed in conduit 592 of exchanger 515, and the first exchanger 312 (FIG. 4) as product hydrogen. The expanded gas from second turbine 518b is returned through conduit 593 to heat exchanger 515 at the midpoint thereof and is withdrawn through conduit 594.

The throttled fluid in separator 545 is separated into a saturated liquid fraction in conduit 546 having a molar composition of 0.98% hydrogen, 98% carbon monoxide and 0.5% methane with the remainder argon and nitrogen, and a saturated vapor fraction in conduit 549 comprising 92% hydrogen and 8% carbon monoxide with approximately 20 ppm methane. The latter gas is combined with the backmix hydrogen from conduit 591 and 117 lb. mole/hr. of the saturated liquid from conduit 546 which is expanded through conduit 547 and valve 548 to a pressure of 22 psia. The resulting cold gas mixture in conduit 551 is consecutively rewarmed in heat exchangers 515 and 312 and forms the other recycle stream. The major fraction of the saturated liquid recovered from separator 545 in conduit 546 is flashed to 18 psia through valve 346a (See FIG. 4), partially warmed and reboiled in heat exchanger 315 and is thereafter fed to separator 361.

Separator 316, operating at 18 psia, separates the partially reboiled fluid into an overhead gas in conduit 364 which constitutes a low pressure recycle stream, and a saturated liquid bottoms in conduit 370 having a molar composition of 0.1% hydrogen, 98.8% carbon monoxide and 0.5% methane with the remainder being nitrogen and argon. This liquid is then pressurized to 87 psia with liquid pump 371, partially rewarmed in second heat exchanger 315 to 101° K., and fed to carbon monoxide methane column 324. The column produces an overhead gas in conduit 332 at 410 lb. mole/hr. of 99.76% carbon monoxide, 0.14% hydrogen and 964 ppm of methane with the remainder nitrogen and argon, and a bottoms liquid in conduit 333 having a molar composition of 65.4% carbon monoxide and 34.5% methane with the remainder nitrogen and argon.

Figure 7:
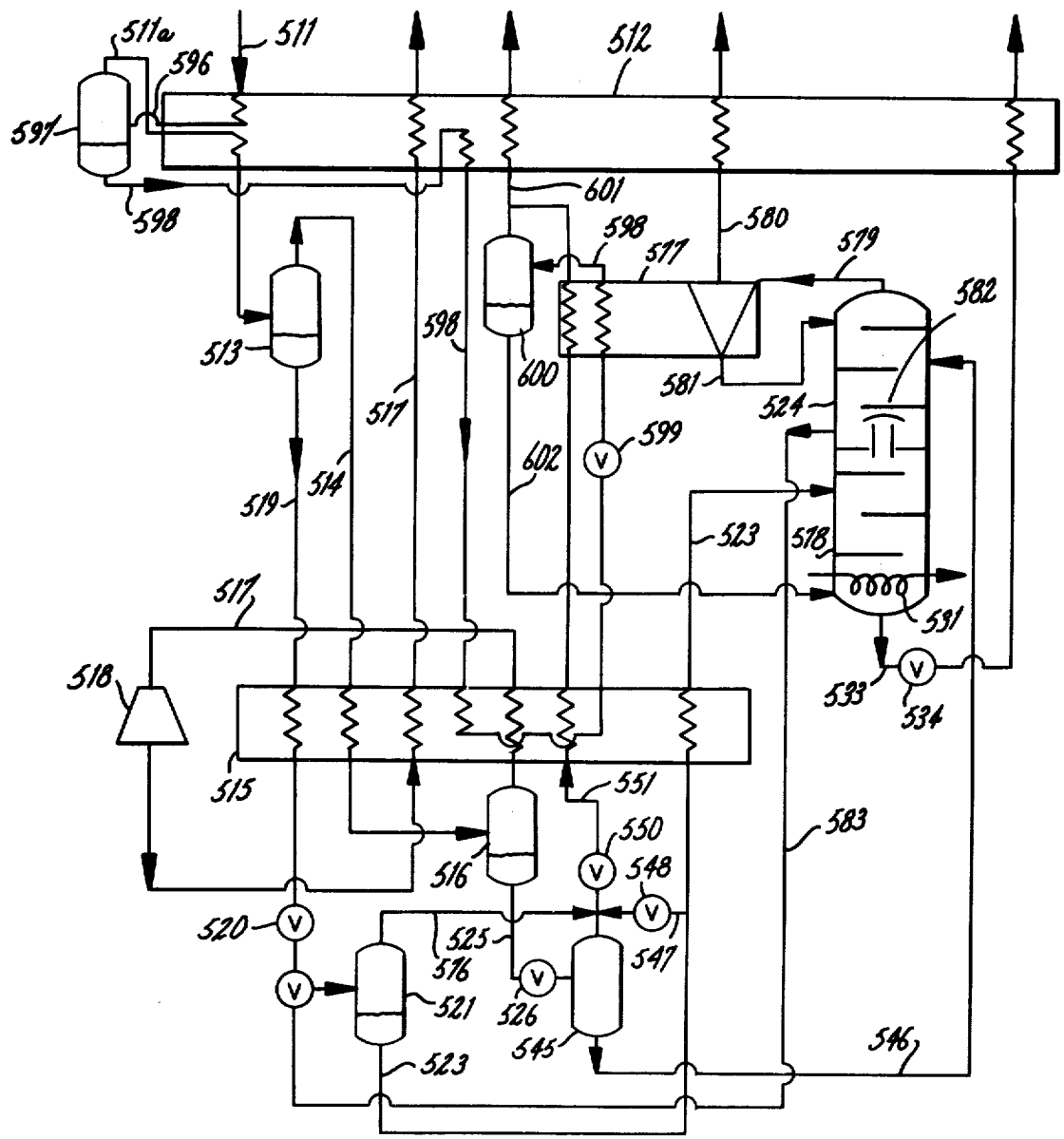
FIG. 7 is a schematic drawing of apparatus suitable for practicing an embodiment of the invention for separating synthesis gas feeds having a carbon monoxide to methane molar ratio below 5.

If the carbon monoxide to methane molar ratio in the synthesis feed gas is below about 5, even the FIG. 5 embodiment requires modifications necessary to insure product purity. Under such conditions, the reflux condenser 477 for the carbon monoxide-methane column 424 cannot be driven by the reboiling, recycle stream. The condenser heat duty becomes excessive due to a higher methane carryover in the overhead gas from the column. This results from the higher methane composition in the feed gas and the lower purity of the carbon monoxide wash liquid recovered from the cold end of the process in fourth separator 445. FIG. 7 illustrates apparatus which may be used to practice an embodiment of the invention which overcomes these problems. In most respects, this process is identical to that previously discussed with reference to FIG. 5. The main difference centers on the development of a liquid of suitable flow rate and temperature to satisfy the heat duty of reflux condenser 577. This is accomplished by partially cooling and condensing the synthesis feed stream from conduit 596 in first heat exchanger 512 to an intermediate temperature and passing the fluid mixture to intermediate separator 597. The liquid portion withdrawn in conduit 598 contains the bulk of the methane in the feed. This liquid is further cooled in heat exchanger 512 and is then subcooled to an appropriate temperature in second heat exchanger 515 such that the throttling of the liquid through valve 599 to a low pressure produces a temperature drop in this stream to near the freezing point of the liquid. This liquid is then partially reboiled in reflux condenser 577 against condensing overhead gas from the carbon monoxide-methane column 524 in conduit 579. The partially reboiled stream still in conduit 598 is then fed to separator 600 wherein a gas fraction in conduit 601 is separated and mixed with the recycle gas stream 551 from separators 521 and 545. The liquid fraction from separator 600 in conduit 602 is fed to the bottom portion of the stripping section 578 of the column 524. The carbon monoxide portion of this stream is reboiled in the lower portion of the stripping section 578 while the major portion of the methane is removed from the bottom of the column through conduit 533.

By this embodiment, the bulk of the methane bypasses the cold end of the stream, as well as the column, so that freezing problems are avoided and the power consumption is reduced significantly.

Although certain embodiments of the invention have been described in detail, it will be appreciated that other embodiments are contemplated along with modifications of the disclosed features, as being within the scope of this invention.

What is claimed is:

1. In the cryogenic separation of a gas mixture comprising hydrogen, carbon monoxide and methane by partial condensation in which the feed gas mixture is provided at super atmospheric pressure above about 300 psia and partially cooled to condense a first liquid fraction and recover a first gas fraction, the first liquid fraction is separated into a carbon monoxide product gas and methane product liquid, the first gas fraction is further cooled for additional partial condensation and separated into a hydrogen enriched gas fraction and a second carbon monoxide rich liquid, the improvement comprising:

(a) treating said first liquid fraction so as to provide a carbon monoxide rich liquid feed for the carbon monoxide-methane separation; (b) further cooling the first gas fraction at about said super atmospheric pressure for said additional partial condensation and separating the same into a second liquid fraction and a second gas fraction as said hydrogen enriched gas; (c) rewarming said second gas fraction as said hydrogen enriched gas fraction by heat exchange initially with the further cooling first gas fraction and thereafter with the partially cooling feed gas mixture; (d) expanding said second liquid fraction to lower pressure between 20 psia and 130 psia, and separating the same into a third liquid fraction and a third gas fraction; (e) providing said third gas fraction at low super atmospheric pressure below about 50 psia; (f) providing a minor portion of a carbon monoxide rich liquid obtained from the cooled feed gas mixture after further cooling, at said low super atmospheric pressure of step (e) and combining the so-provided minor portion with the third gas fraction of (e) to form a recycle gas mixture; (g) rewarming said recycle gas mixture by heat exchange initially with the further cooling first gas fraction and thereafter with the partially cooling feed gas mixture; and (h) flowing at least a major portion of said third liquid fraction to the carbon monoxide-methane separation.

2. A method according to claim 1 in which said first liquid fraction of (a) is throttled to lower super atmospheric pressure between 20 psia and 130 psia, separated into a lower pressure liquid fraction as said carbon monoxide rich liquid feed, and a lower pressure gas fraction which is warmed by heat exchange with said feed gas mixture during the partial cooling thereof.

3. A method according to claim 1 in which said first liquid fraction of (a) is throttled to lower super atmospheric pressure, separated into a lower pressure liquid fraction and a lower pressure gas fraction with the latter being warmed by heat exchange with said feed gas mixture during the partial cooling thereof, said lower pressure liquid fraction is further cooled, again throttled to still lower super atmospheric pressure and separated into a still lower pressure gas fraction and a still lower pressure liquid fraction, said still lower pressure gas fraction is first partially warmed by heat exchange with both the further cooling and additionally condensing first gas fraction and the further cooling lower pressure liquid fraction and thereafter further warmed by heat exchange with said feed gas mixture during the partial cooling thereof, at least a major part of said still lower pressure liquid fraction is partially reboiled by heat exchange with both the further cooling and additionally condensing first gas fraction and the further cooling lower pressure liquid fraction, and at least part of the partially reboiled still lower pressure liquid fraction is passed to the carbon monoxide-methane separation as at least part of said carbon monoxide rich liquid feed.

4. A method according to claim 3 in which another part of said partially reboiled still lower pressure liquid fraction is separated into a gas stream which is warmed by heat exchange with said feed gas mixture during the partial cooling thereof, and a liquid fraction which is passed to the carbon monoxidemethane separation as the remainder of said carbon monoxide rich liquid feed.

5. A method according to claim 1 in which said first liquid fraction of (a) is throttled to lower super atmospheric pressure, separated into a lower pressure liquid fraction and a lower pressure gas fraction with the latter being warmed by heat exchange with said feed gas mixture during the partial cooling thereof, said lower pressure liquid fraction is further cooled, again throttled to still lower super atmospheric pressure and separated into a still lower pressure gas fraction and a still lower pressure liquid fraction said still lower pressure gas fraction is first partially warmed by heat exchange with both the further cooling and additionally condensing first gas fraction and the further cooling lower pressure liquid fraction and thereafter further warmed by heat exchange with said feed gas mixture during the partial cooling thereof, at least a major part of said still lower pressure liquid fraction is partially reboiled by heat exchange with both the further cooling and additionally condensing first gas fraction and the further cooling lower pressure liquid fraction but the partially reboiled fluid is withdrawn from an intermediate temperature level of the further cooling heat exchange and separated into a partially rewarmed still lower pressure gas fraction and a partially rewarmed still lower pressure liquid fraction, said partially rewarmed still lower pressure gas fraction is further rewarmed by heat exchange with said feed gas mixture during the partial cooling thereof, said partially rewarmed still lower pressure liquid fraction is returned to about said intermediate temperature level and such returned liquid fraction is further reboiled by additional heat exchange with both the further cooling and additionally condensing first gas fraction and the further cooling lower pressure liquid fraction, and the further reboiled still lower pressure liquid fraction is passed to the carbon monoxide-methane separation as said carbon monoxide rich liquid feed.

6. A method according to claim 1 in which said carbon monoxide-methane separation comprises an upper rectification section to which said third liquid fraction is flowed and a lower stripping section, said first liquid fraction of (a) is further cooled, throttled to lower super atmospheric pressure and separated into a lower pressure gas fraction and a lower pressure liquid fraction, said lower pressure gas fraction is rewarmed by heat exchange with the further cooling first liquid fraction and the further cooling first gas and thereafter by heat exchange with the partially cooling feed gas, at least a major part of said lower pressure liquid fraction is partially reboiled by heat exchange with the further cooling first liquid fraction and the further cooling first gas, the partially reboiled lower pressure liquid fraction is passed to said stripping section as said carbon monoxide rich liquid feed, overhead gas from said upper rectification section is cooled and partially condensed by heat exchange with said recycle gas mixture between the rewarming and further rewarming of (g), the condensate is returned to said upper rectification section as reflux liquid, the uncondensed gas is rewarmed by heat exchange with said partially cooling feed gas mixture and discharged as said carbon monoxide product gas, and the liquid from the lower end of said upper rectifying section is withdrawn and passed to the further cooled lower pressure liquid-gas fraction separation.

7. A method according to claim 6 in which a liquid-gas mixture is withdrawn from an intermediate temperature level of the feed gas partial cooling-condensation, separated into an intermediate temperature gas which is returned to the partial cooling step and an intermediate temperature methane enriched liquid which is further cooled and thereafter subcooled, throttling the subcooled methane enriched liquid and partially reboiling the throttled liquid by heat exchange with said overall gas from said upper rectification section, separating the partially reboiled fluid into a gas fraction which is warmed by heat exchange with the partially cooling feed gas mixture and a liquid which is introduced to the lower stripping section of said carbon monoxide-methane separation.

8. A method according to claim 1 in which the carbon monoxide rich liquid of (e) is provided by diverting a minor part of said third liquid fraction from (e).

9. A method according to claim 3 in which the carbon monoxide rich liquid of (e) is provided by diverting a minor part of said lower pressure liquid fraction prior to the partial reboiling.

10. A method according to claim 1 in which a minor part of said second gas fraction from (b) is diverted and mixed with said third vapor fraction of (e) for further cooling prior to said rewarming of (g).

* * * * *